(12) United States Patent
Zhao et al.

(10) Patent No.: US 12,311,001 B2
(45) Date of Patent: May 27, 2025

(54) USE OF EXTRACELLULAR VESICLES OF RHIZOMA DRYNARIAE IN PREPARATION OF MEDICINE FOR TREATING ORTHOPEDIC DISEASES

(71) Applicant: THE THIRD AFFILIATED HOSPITAL OF GUANGZHOU UNIVERSITY OF CHINESE MEDICINE, Guangzhou (CN)

(72) Inventors: Kewei Zhao, Guangzhou (CN); Qing Zhao, Guangzhou (CN)

(73) Assignee: THE THIRD AFFILIATED HOSPITAL OF GUANGZHOU UNIVERSITY OF CHINESE MEDICINE, Guangzhou (CN)

( * ) Notice: Subject to any disclaimer, the term of this patent is extended or adjusted under 35 U.S.C. 154(b) by 0 days.

(21) Appl. No.: 18/559,889

(22) PCT Filed: Aug. 16, 2022

(86) PCT No.: PCT/CN2022/112697
§ 371 (c)(1),
(2) Date: Nov. 9, 2023

(87) PCT Pub. No.: WO2023/155398
PCT Pub. Date: Aug. 24, 2023

(65) Prior Publication Data
US 2025/0000923 A1    Jan. 2, 2025

(30) Foreign Application Priority Data
Feb. 16, 2022    (CN) .......................... 202210141049.3

(51) Int. Cl.
*A61K 36/00* (2006.01)
*A61K 36/126* (2006.01)
*A61K 45/06* (2006.01)

(52) U.S. Cl.
CPC .......... *A61K 36/126* (2013.01); *A61K 45/06* (2013.01); *A61K 2236/31* (2013.01); *A61K 2236/53* (2013.01)

(58) Field of Classification Search
CPC .................................................. A61K 36/126
See application file for complete search history.

(56) References Cited

U.S. PATENT DOCUMENTS

2016/0045448 A1    2/2016    Zhang

FOREIGN PATENT DOCUMENTS

| CN | 110227066 A | 9/2019 |
|---|---|---|
| CN | 114344348 A | 4/2022 |

OTHER PUBLICATIONS

International Search Report, dated Nov. 3, 2022, issued in corresponding International Patent Application No. PCT/CN2022/112697.
Chen, Yiqing et al., "Advances in exosomes on bone remodeling and osteoporosis," Chinese Journal of Osteoporosis, vol. 26, No. 1, Jan. 2020, pp. 129-132. English Abstract.
Xie, Fei et al., "Research of the mechanism and the role of exosomes in bone regeneration," Chinese Journal of Osteoporosis, vol. 26, No. 5, May 2020, pp. 737-739. English Abstract.
Guo, Lan et al., "Study on the relationship between the theory of 'kidney main bone producing marrow' and osteoporosis from exosome," Chinese Journal of Osteoporosis, vol. 26, No. 12, Dec. 2020, pp. 1852-1855. English Abstract.
Office Action, dated Jun. 9, 2022, issued in corresponding CN Patent Application No. 202210141049.3.
Office Action, dated Aug. 31, 2022, issued in corresponding CN Patent Application No. 202210141049.3.
Gao, Wenjing et al., "Research Progress of Exosomes as New Active Components of Traditional Chinese Medicine," World Science and Technology—Modernization of Traditional Chinese Medicine, vol. 21, No. 9, Dec. 2019, pp. 1869-1876. English Abstract.
Notification to Grant Patent Right for Invention, dated Nov. 14, 2022, issued in corresponding CN Application No. 202210141049.3.

*Primary Examiner* — Qiuwen Mi
(74) *Attorney, Agent, or Firm* — Kathleen D. Rigaut; Howson & Howson LLP

(57) ABSTRACT

Use of extracellular vesicles of Rhizoma Drynariae in the preparation of a medicine for treating orthopedic diseases. The extracellular vesicles are extracted from the traditional Chinese medicine Rhizoma Drynariae, so that proliferation and differentiation of the bone marrow mesenchymal stem cells can be promoted, and the bone targeting property is achieved; in addition, various functional components which are the same as those of Rhizoma Drynariae are contained, so that the potential of treating orthopedic diseases is proved. Therefore, the extracellular vesicles of Rhizoma Drynariae can be applied to the preparation of a medicine for treating orthopedic diseases.

1 Claim, 4 Drawing Sheets

Specification includes a Sequence Listing.

USE OF EXTRACELLULAR VESICLES OF RHIZOMA DRYNARIAE IN PREPARATION OF MEDICINE FOR TREATING ORTHOPEDIC DISEASES

CROSS-REFERENCE TO RELATED APPLICATION(S)

This application is a § 371 of International Application No. PCT/CN2022/112697, filed Aug. 16, 2022, which claims priority to Chinese Patent Application No. 202210141049.3, filed Feb. 16, 2022, the entire contents of each being incorporated by reference as though set forth in full.

TECHNICAL FIELD

The present application belongs to the technical field of biomedical, and relates to use of extracellular vesicles of Rhizoma Drynariae in preparation of medicines for treating orthopedic diseases.

BACKGROUND

Rhizoma Drynariae belongs to a root of *Drymotaenium fortunei* (Kze.) J. Smith and can be harvested throughout the year. Rhizoma Drynariae has a function of relieving pains and strengthening bones and is a common traditional Chinese medicine for clinically treating osteoporosis (OP). Rhizoma Drynariae mainly contains a flavone compound, and modern pharmacological studies have shown that Rhizoma Drynariae has effects of anti-OP, anti-inflammation and repairing a bone injury. Multiple studies have found that Rhizoma Drynariae can promote bone formation or inhibit bone resorption by regulating bone metabolism-related cells, thereby achieving an anti-OP effect. For example, Rhizoma Drynariae has an effect of promoting the proliferation and osteogenic differentiation of BMSCs (bone marrow mesenchymal stem cells) and an estrogen-like effect of traditional Chinese medicine so that a function of the bone metabolism-related cells can be affected through an ER (estrogen receptor) pathway to achieve anti-OP. At present, Rhizoma Drynariae is mainly used for treatment through being used as a medicine as a whole or in a form of monomer and has the disadvantages of low oral bioavailability and no selective distribution in vivo, resulting in a limitation of Rhizoma Drynariae in clinical application. Therefore, it is conducive to the establishment of a modern system of traditional Chinese medicine to find a more effective manner to exert the effects of the traditional Chinese medicine Rhizoma Drynariae.

Exosomes are extracellular vesicles (EVs) with a bimolecular phospholipid structure secreted by many different types of cells and are widely found in various body fluids. The exosomes contain a variety of biological ingredients including mRNA, miRNA, proteins and lipids and can participate in the exchange of substances between cells, thereby affect a function of the cells. In recent years, with the rapid development of separation technology and the exosomes, many people have been able to separate EVs with a particle size of about 30-500 nm from a plant. These plant-derived EVs have a targeting property and biological activity and can transfer information between different species, thereby regulating a biological function of an organism. For example, *ginseng*-derived nanoparticles, which can target a liver and a spleen, promote the apoptosis of melanoma cells by promoting the polarization of a phenotype M2 of tumor-associated macrophages to M1. However, no literature has reported EVs derived from Rhizoma Drynariae. Therefore, it is still unknown whether the extraction of EVs from the traditional Chinese medicine Rhizoma Drynariae is feasible and whether the extracted extracellular vesicles of Rhizoma Drynariae (DREVs) have the biological activity or a related function of the traditional Chinese medicine Rhizoma Drynariae.

Therefore, what becomes an urgent problem to be solved in the art is that how to provide a method for extracting extracellular vesicles from a traditional Chinese medicine Rhizoma Drynariae and deeply study a function of the extracted DREVs to discover the application potential of the extracellular vesicles of Rhizoma Drynariae in treating an orthopedic disease.

SUMMARY

The present application provides use of extracellular vesicles of Rhizoma Drynariae in preparation of a medicine for treating an orthopedic disease.

In a first aspect, the present application provides use of extracellular vesicles of Rhizoma Drynariae in preparation of a medicine for treating an orthopedic disease.

In the present application, the extracellular vesicles are creatively extracted from the traditional Chinese medicine Rhizoma Drynariae, and a function of the extracellular vesicles is studied. It is found that the extracellular vesicles can promote the proliferation and differentiation of BMSCs, have a bone targeting property in vivo and contain the same multiple functional ingredients as Rhizoma Drynariae, proving that the extracellular vesicles have the potential to treat the orthopedic disease and can be applied to the preparation of the medicine for treating the orthopedic disease.

Preferably, the extracellular vesicles of Rhizoma Drynariae contain naringin, eriodictyol, cinnamic acid, naringenin, prunin, caffeic acid, sinapinic acid, afzelin, secoisolariciresinol, narirutin and kaempferol.

Preferably, the extracellular vesicles of Rhizoma Drynariae are extracted through an extraction method including the following steps:
(1) juicing Rhizoma Drynariae, filtering, collecting a filtrate, centrifuging to remove impurities and collecting a supernatant; and
(2) centrifuging the supernatant at a speed of 100000-200000 g for 60-120 min and collecting a precipitate to obtain the extracellular vesicles of Rhizoma Drynariae.

Specific values in the above 100000-200000 g include, for example, 100000 g, 110000 g, 120000 g, 130000 g, 140000 g, 150000 g, 160000 g, 170000 g, 180000 g, 190000 g, 200000 g or the like.

Specific values in the above 60-120 min include, for example, 60 min, 65 min, 70 min, 75 min, 80 min, 85 min, 90 min, 95 min, 100 min, 105 min, 110 min, 115 min, 120 min or the like.

Preferably, the configuration in step (1) includes at least three centrifugations.

Preferably, the centrifugation in step (1) includes three centrifugations, where a first centrifugation is performed at a speed of 100-500 g, a second centrifugation is performed at a speed of 1000-3000 g, and a third centrifugation is performed at a speed of 8000-12000 g.

Specific values in the above 100-500 g include, for example, 100 g, 150 g, 200 g, 250 g, 300 g, 350 g, 400 g, 450 g, 500 g or the like.

Specific values in the above 1000-3000 g include, for example, 1000 g, 1200 g, 1500 g, 1700 g, 2000 g, 2200 g, 2500 g, 2700 g, 3000 g or the like.

Specific values in the above 8000-12000 g include, for example, 8000 g, 8500 g, 9000 g, 9500 g, 10000 g, 10500 g, 11000 g, 11500 g, 12000 g or the like.

Preferably, the centrifugations in step (1) are each independently performed for 5-30 min, for example, 5 min, 10 min, 15 min, 20 min, 25 min, 30 min or the like.

Preferably, a type of the orthopedic disease includes any one of osteoporosis, fracture or osteoarthritis.

Preferably, a dosage form of the medicine includes any one of a tablet, an electuary, a capsule, a solution, an aerosol, a spray, an ointment or a film.

Preferably, the medicine further includes a pharmaceutically acceptable adjuvant.

Preferably, the adjuvant includes any one or a combination of at least two of a diluent, a flavoring agent, an adhesive or a filler, wherein the combination of the at least two of the above may be, for example, a combination of the diluent and the flavoring agent, a combination of the adhesive and the filler or a combination of the flavoring agent and the adhesive, and any other combinations are also possible.

In a second aspect, the present application provides use of extracellular vesicles of Rhizoma Drynariae in preparation of a bone targeting preparation.

In the present application, it is creatively found that the extracellular vesicles of Rhizoma Drynariae have a bone targeting property in an animal, and this finding can be further applied to the preparation of the bone targeting preparation for studying pathogenesis of an orthopedic disease and treating a related disorder.

Preferably, the bone targeting preparation further includes other medicines for treating an orthopedic disease, and the other medicines for treating the orthopedic disease are loaded in the extracellular vesicles of Rhizoma Drynariae.

The other medicines for treating the orthopedic disease include, for example, a calcium preparation, an estrogen medicine, calcitonin, a diphosphate medicine and teriparatide.

In a third aspect, the present application provides use of extracellular vesicles of Rhizoma Drynariae in preparation of a BMSC proliferation promoter.

In a fourth aspect, the present application provides use of extracellular vesicles of Rhizoma Drynariae in preparation of a BMSC osteogenic differentiation promoter.

In the present application, the extracellular vesicles are creatively extracted from the traditional Chinese medicine Rhizoma Drynariae, and a function of the extracellular vesicles is studied. It is found that the extracellular vesicles can promote the proliferation and osteogenic differentiation of BMSCs. Original BMSCs are bone marrow stromal stem cells, which are a subset of cells found in a bone marrow stroma of a mammal with the differentiation potential of differentiating into bones, cartilages, fats, nerves and myoblasts. The original BMSCs not only have a mechanical support effect on hematopoietic stem cells (HSCs) in bone marrow, but also secrete multiple growth factors (such as IL-6, IL-11, LIF, M-CSF and SCF) to support hematopoiesis. The original BMSCs may be applied to HSC transplantation, repair of a tissue injury and treatment of an autoimmune disease, and may also be used as a vector for gene therapy. Therefore, this discovery of the present application can be further applied to studies on related mechanisms, such as HSC transplantation, repair of a tissue injury, an autoimmune disease, gene therapy, and the development of a related medicine or vector.

In a fifth aspect, the present application provides use of extracellular vesicles of Rhizoma Drynariae in preparation of an estrogen receptor signal pathway agonist.

In the present application, the extracellular vesicles are creatively extracted from the traditional Chinese medicine Rhizoma Drynariae, and a function of the extracellular vesicles is studied. It is found that the extracellular vesicles can upregulate the mRNA expression of related genes (ERα and ERβ) of the ER (estrogen receptor) pathway, thereby achieving the regulation of the ER pathway. Therefore, the extracellular vesicles can be used for the preparation of the estrogen receptor signal pathway agonist.

Any numerical range described in the present application includes not only the above-listed point values but also any point values within the numerical range which are not listed. Due to the limitation of space and the consideration of simplicity, specific point values included in the range are not exhaustively listed in the present application.

Compared with the prior art, the present application has the beneficial effects described below.

In the present application, the extracellular vesicles are creatively extracted from the traditional Chinese medicine Rhizoma Drynariae, and the function of the extracellular vesicles is studied. It is found that the extracellular vesicles can promote the proliferation and differentiation of the BMSCs, have the bone targeting property and contain the same multiple functional ingredients as Rhizoma Drynariae, proving that the extracellular vesicles have the potential to treat the orthopedic disease and can be applied to the preparation of the medicine for treating the orthopedic disease. Therefore, the present application creatively provides the use of the extracellular vesicles of Rhizoma Drynariae to the preparation of the BMSC proliferation promoter, the use of the extracellular vesicles of Rhizoma Drynariae to the preparation of the bone targeting preparation and the use of the extracellular vesicles of Rhizoma Drynariae to the preparation of the medicine for treating the orthopedic disease.

No literature has reported on the extraction method and functional study of the extracellular vesicles in Rhizoma Drynariae. In the present application, the extracellular vesicles in Rhizoma Drynariae are first extracted and deeply studied for the first time. The present application provides a new strategy for studying plant-derived extracellular vesicles and studying and treating the orthopedic disease.

DETAILED DESCRIPTION

Technical solutions of the present application are further described below through embodiments. Those skilled in the art are to understand that the examples described herein are used for a better understanding of the present application and are not to be construed as specific limitations to the present application.

Rhizoma Drynariae involved in the following examples is purchased from Zhaoqing, Guangdong Province, and identified as a root of *Drynaria fortunei* (Kunze) J.Sm. by the Traditional Chinese Medicine Pharmacy of the Third Affiliated Hospital of Guangzhou University of Chinese Medicine.

Example 1

Extraction of DREVs

This example provides a method for extracting DREVs. The method includes the steps described below.

500 g of fresh Rhizoma Drynariae was taken and thoroughly cleaned with sterile water, cut into small pieces and juiced. After filtration, the supernatant was collected in a clean 50 mL centrifuge tube and centrifuged at 300 g for 10 min at 4° C. to remove floating cells. The supernatant was collected in a 50 mL centrifuge tube and centrifuged at 2000 g for 20 min at 4° C. to remove dead cells and falling vesicles. The supernatant was collected in a 50 mL centrifuge tube and centrifuged at 10000 g for 30 min at 4° C. to remove dead cells, falling vesicles and apoptotic bodies. The supernatant was collected in a special centrifuge tube for a differential ultrahigh-speed centrifuge and centrifuged at 135000 g for 70 min at 4° C., and the supernatant was discarded. A precipitate was resuspended in a pre-cooled 1×PBS buffer and filtered by using a 0.22 μm disposable syringe filter. Finally, the DREVs was collected in a sterilized EP tube and stored in a refrigerator at −80° C. for later use.

Example 2

Characterization of DREVs

The morphology, particle size and content of the DREVs extracted in Example 1 were characterized.

Figure 1:
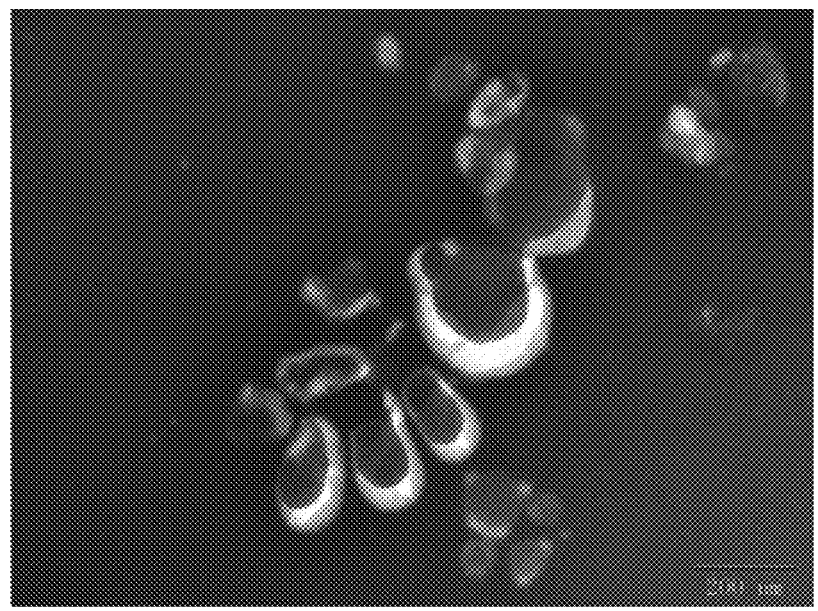
FIG. 1 is an image of extracellular vesicles of Rhizoma Drynariae observed under a transmission electron microscope.

The morphology of the DREVs was observed under a transmission electron microscope. It can be observed that the DREVs are round or oval in shape, have a typical cup-shaped vesicle structure and a complete cell membrane structure and have a particle size of between 0-300 nm (see FIG. 1 with a scale of 200 nm), which conforms to a particle size range of EVs reported in a literature and proves the successful extraction of the EVs.

The particle size distribution of the DREVs was analyzed by using a nanoparticle tracking analyzer. It is found that the DREVs have a particle size distributed between 0-300 nm (the result is the same as that observed under the transmission electron microscopy) and a concentration of $1.04 \times 10^9$ particles/mL, which further proves the successful extraction of the EVs.

Figure 2:
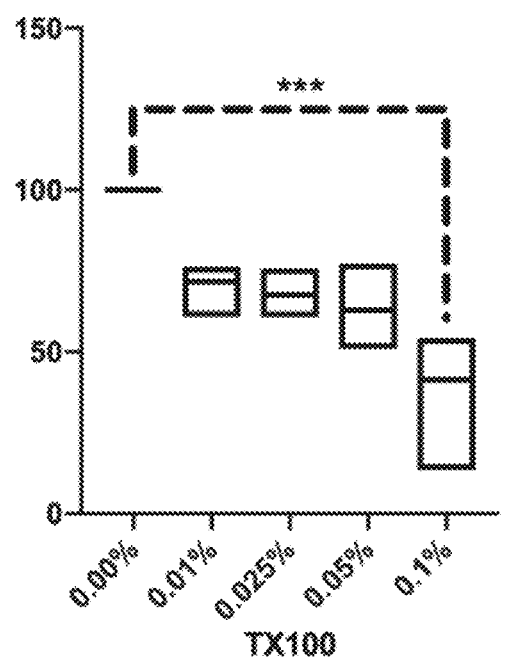
FIG. 2 is a diagram illustrating change results of the number of particles of extracellular vesicles of Rhizoma Drynariae treated with different concentrations of Triton X-100.

Different concentrations of surfactants Triton X-100 (TX100) which impair the integrity of membranes were used for dissolving membranes of the DREVs, respectively. Then, a change in the number of particles of DREVs was tested by using a nanoflow detector. The results show that the number of particles of DREVs gradually decreases as the concentration of Triton X-100 increases. Compared with a group not using Triton X-100, the number of particles of DREVs in a group using 0.1% Triton X-100 is significantly decreased, and a difference has a statistical significance (in FIG. 2, $P<0.001$, and the ordinate in FIG. 2 is a percentage of the number of particles of DREVs after the treatment of Triton X-100 to the number of untreated particles of DREVs). This result proves that the extracted DREVs have a complete membrane structure, that is, proves the successful extraction of the EVs.

Figure 3:
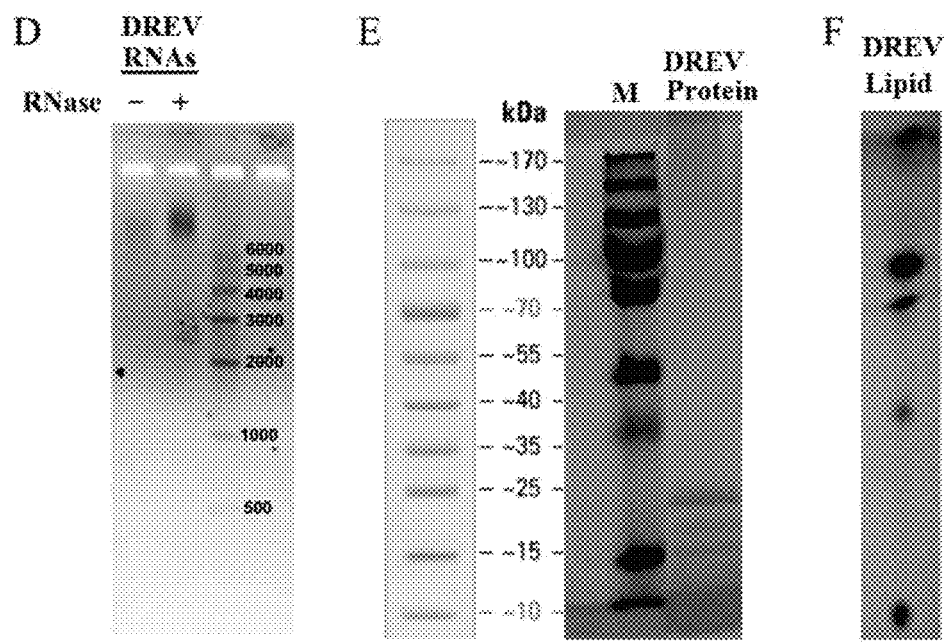
FIG. 3 is a diagram illustrating detection results of RNA, proteins and lipids in extracellular vesicles of Rhizoma Drynariae, where figure D is a diagram illustrating detection results of RNA in the extracellular vesicles of Rhizoma Drynariae, figure E is a diagram illustrating detection results of the proteins in the extracellular vesicles of Rhizoma Drynariae, and figure F is a diagram illustrating detection results of the lipids in the extracellular vesicles of Rhizoma Drynariae.

RNA, proteins and lipids in the DREVs were detected through methods of agarose gel electrophoresis, Coomassie brilliant blue staining and TLC (thin-layer chromatography), respectively. The results are shown in FIG. 3 (D, E and F), where the M band in FIG. 3 represent a protein Marker band. The results show that the DREVs contain high-molecular-weight RNA sensitive to degradation of ribonuclease (RNase), proteins with a molecular weight of about 15-25 kDa and different types of lipids.

Example 3

Exploring Promotion Effects of DREVs on Proliferation and Differentiation of h-BMSCs To understand the biological activity of the DREVs, an effect of the DREVs on the proliferation of the h-BMSCs was detected through a CCK8 method.

Experimental method: the h-BMSCs were cultured by using DMEM-F12 medium+10% fetal bovine serum (FBS)+1% anti-penicillin-streptomycin under 5% $CO_2$ (standard atmospheric pressure) at 37° C. When a density of adherent cells reached 80%-90%, the cells were digested by trypsin, and the cells were collected and counted. The cells were inoculated in a 96-well plate according to a cell density of $3 \times 10^3$ cells/cm². A protein content of the DREVs was detected by using BCA kit. Different concentrations of DREVs were co-cultured with the h-BMSCs, and the concentration of each group was marked. The concentrations may be divided into four groups: 15 μg/mL DREVs, 20 μg/mL DREVs, 30 μg/mL DREVs and a control group where no DREV was added, respectively. An absorbance at 450 nm was measured after 12 h, 24 h and 48 h of culture according to an operation in a specification of a CCK-8 kit.

Figure 4:
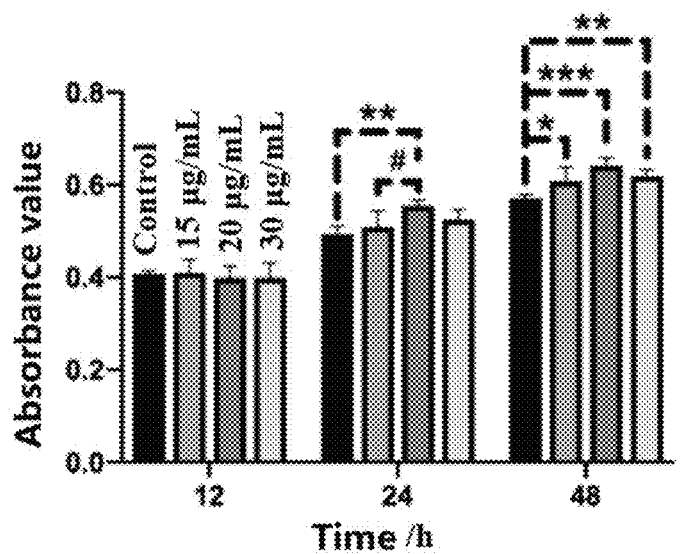
FIG. 4 is a diagram illustrating results of effects of different concentrations of extracellular vesicles of Rhizoma Drynariae on the proliferation of human bone marrow mesenchymal stem cells (h-BMSCs).

The results are shown in FIG. 4. After the 48 h of culture, compared with the control group, the 15 μg/mL, 20 μg/mL and 30 μg/mL DREVs all promote the proliferation of the h-BMSCs, and a difference has a statistical significance ($P<0.05$). The 20 μg/mL DREVs have a best effect on promoting the proliferation so that the concentration is the best. After the 24 h of culture, a difference is between the group of 15 μg/mL DREVs and the group of 20 μg/mL DREVs, and the difference has a statistical significance ($P<0.05$).

An effect of the DREVs on the osteogenic differentiation of the h-BMSCs was detected through qRT-PCR.

An experimental method is described below.

The h-BMSCs were purified, cultured, grown to an appropriate density and digested by trypsin, and the cells were collected and counted. The cells were inoculated in a six-well plate according to a cell density of $2\times10^5$ cells/m², and the six-well plate was placed in an incubator for culture. When the cell density was increased to 80%, liquids in the wells were completely drawn and replaced with osteogenic differentiation inducing mediums of corresponding groups. The cells were divided into two groups: a control group and an experimental group. In the control group, an osteogenic differentiation inducing liquid was added to h-BMSCs to induce differentiation, and in the experimental group, 20 μg/mL DREVs stimulate h-BMSCs, and an osteogenic differentiation inducing liquid was added to the h-BMSCs to induce differentiation. After this, the osteogenic differentiation inducing mediums of the corresponding groups were replaced once every three days. On days 0, 1, 3, 6 and 9 of inducing osteogenic differentiation, the cells were collected by using a TRIzol lysate, placed in sterilized EP tubes and marked, and qRT-PCR was performed to detect the expression of osteogenic differentiation-related genes (ALP and BMP2).

Primer sequences of the related genes are as follows:
Alp Sequences:

SEQ ID NO. 1:
ACCACCACGAGAGTGAACCA (5'->3')

SEQ ID NO. 2:
CCCTGACCATGAGTCTGTTGC (5'->3')

Bmp2 Sequences:

SEQ ID NO. 3:
ACTACCAGAAACGAGTGGGAA (5'->3')

SEQ ID NO. 4:
TCCAAAAGGCTCTTGTCTACG (5'->3')

Gapdh Sequences:

SEQ ID NO. 5:
ACAACTTTGGTATCGTGGAAGG (5'->3')

SEQ ID NO. 6:
CTTTGACACCGCACTACCG (5'->3')

A procedure for an amplification reaction: for 10 min at 95° C. (pre-denaturation), for 10 s at 95° C. (denaturation), for 15 s at 60° C. (annealing and fluorescence collection) and for 20 s at 72° C. (extension), a total of 40 cycles; a melting curve: for 15 s at 95° C., for 1 min at 60° C., for 15 s at 95° C. and for 15 s at 60° C.

At the end of the amplification reaction experiment, whether an amplification curve and a dissolution curve were normal curves was observed, and under the normal curves, the specificity of different products was detected through a melting curve analysis. An internal reference gene was a GAPDH gene, and each sample was repeatedly detected three times to reduce a systematic error, and a relative quantification (RQ) of each sample gene was determined through a comparative Ct method. A Ct value of each sample gene was analyzed, the result was represented by a relative level of the comparison between the each sample gene and the internal reference GAPDH gene, and finally, a relative expression level of the each sample gene was calculated by using a $2^{-\Delta\Delta CT}$ formula.

Figure 5:
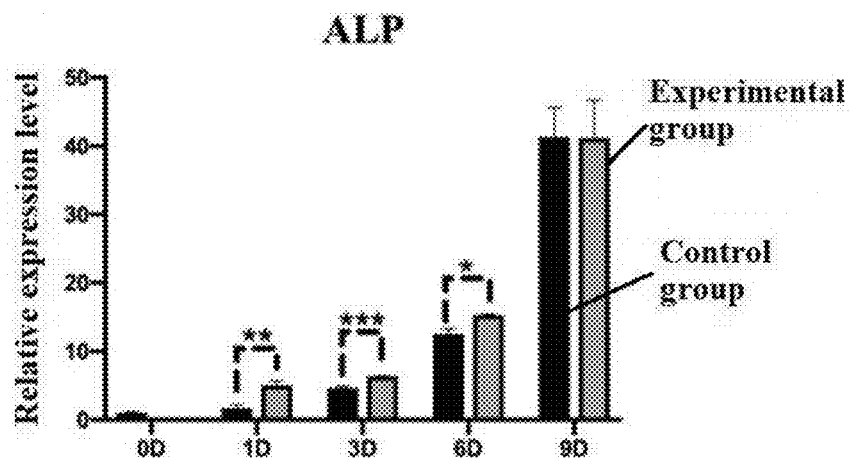
FIG. 5 is a diagram illustrating results of effects of extracellular vesicles of Rhizoma Drynariae on the expression of ALP.
Figure 6:
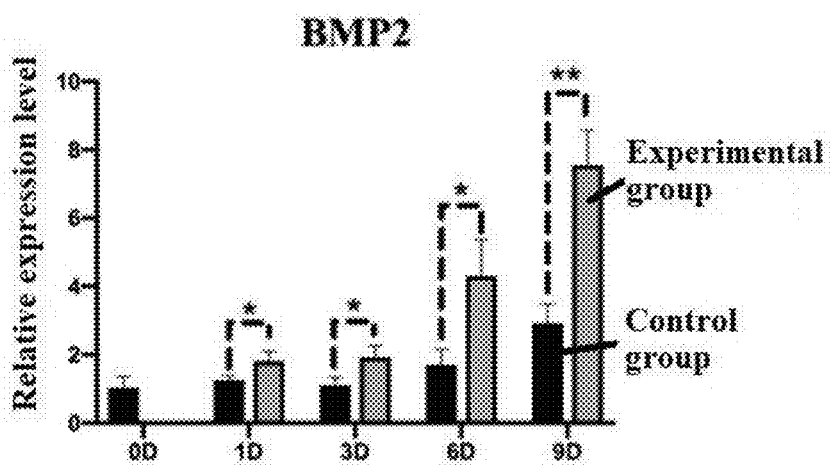
FIG. 6 is a diagram illustrating results of effects of extracellular vesicles of Rhizoma Drynariae on the expression of BMP2.

The results show that compared with the control group, the 20 μg/mL DREVs can upregulate the expression of the osteogenic phenotype gene ALP during the osteogenic differentiation of the h-BMSCs and the difference results on days 1, 3 and 6 have statistical significances, respectively (in FIG. 5, the ordinate is a relative expression level of the gene, and $P<0.05$). Compared with the control group, the 20 μg/mL DREVs can upregulate the expression of the osteogenic phenotype gene BMP2 during the osteogenic differentiation of the h-BMSCs, and the difference results on days 1, 3, 6 and 9 have statistical significances, respectively (in FIG. 6, the ordinate is a relative expression level of the gene, and $P<0.05$).

Figure 7:
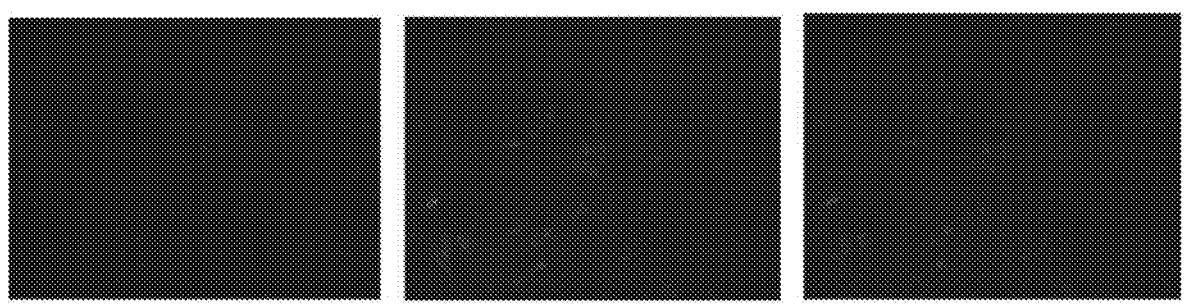
FIG. 7 is an image illustrating results of exploring the internalization and absorption of extracellular vesicles of Rhizoma Drynariae by h-BMSCs.

To exert the effect, the EVs need to be taken up by target cells first and then affect a related function of the target cells. Therefore, to prove that the DREVs can be internalized and absorbed by the h-BMSCs, the DREVs were marked with a lipophilic fluorescent dye Dil dye (red), and the marked DREVs were co-cultured with the h-BMSCs. After six hours, cell nuclei of the h-BMSCs were stained by using a cell nucleus dye Hoechst 33342 (blue) to observe a specific localization of the Dil-DREVs after the Dil-DREVs were internalized and absorbed. The results show that under a fluorescence microscope, the cell nuclei show blue fluorescence, and the Dil-DREVs show red fluorescence and mostly located in cytoplasm of the h-BMSCs (FIG. 7), which proves that the DREVs can be internalized and absorbed by the h-BMSCs.

Example 4

Exploring Bone Targeting Property of DREVs in Animal

The preparation of a solution of DiR-DREVs: 200 μL DREVs were taken, placed in a sterilized EP tube and marked, according to a requirement of a manufacturer's specification, 5 μL DiR staining solution was added, and finally, a phosphate-buffered saline (PBS) buffer was added to dilute to 1000 μL, uniformly mixed and stained for 20 minutes in the dark. After 20 minutes, the mixture was centrifuged at 135000×g for 70 min at 4° C., and the supernatant was discarded. After a precipitate was resuspended in a PBS buffer, centrifugation was repeated twice to three times to wash an excess staining solution. After the last centrifugation, a precipitate was resuspended in 100 μL PBS buffer to obtain the solution of DiR-DREVs, which was stored in a refrigerator at −80° C. for later use.

A 100 μL solution of DiR-DREVs was injected into female C57BL/6J mice through different administration routes (tail vein injection and intraperitoneal injection). 100

μL 1×PBS was administered as a blank control group, and 100 μL DiR staining solution diluted with PBS (the DiR staining solution had a concentration of 20 μL/mL) was administered as a positive control group. Fluorescence imaging was performed at 6 hours, 24 hours, 48 hours and 72 hours after the administration.

Figure 8:
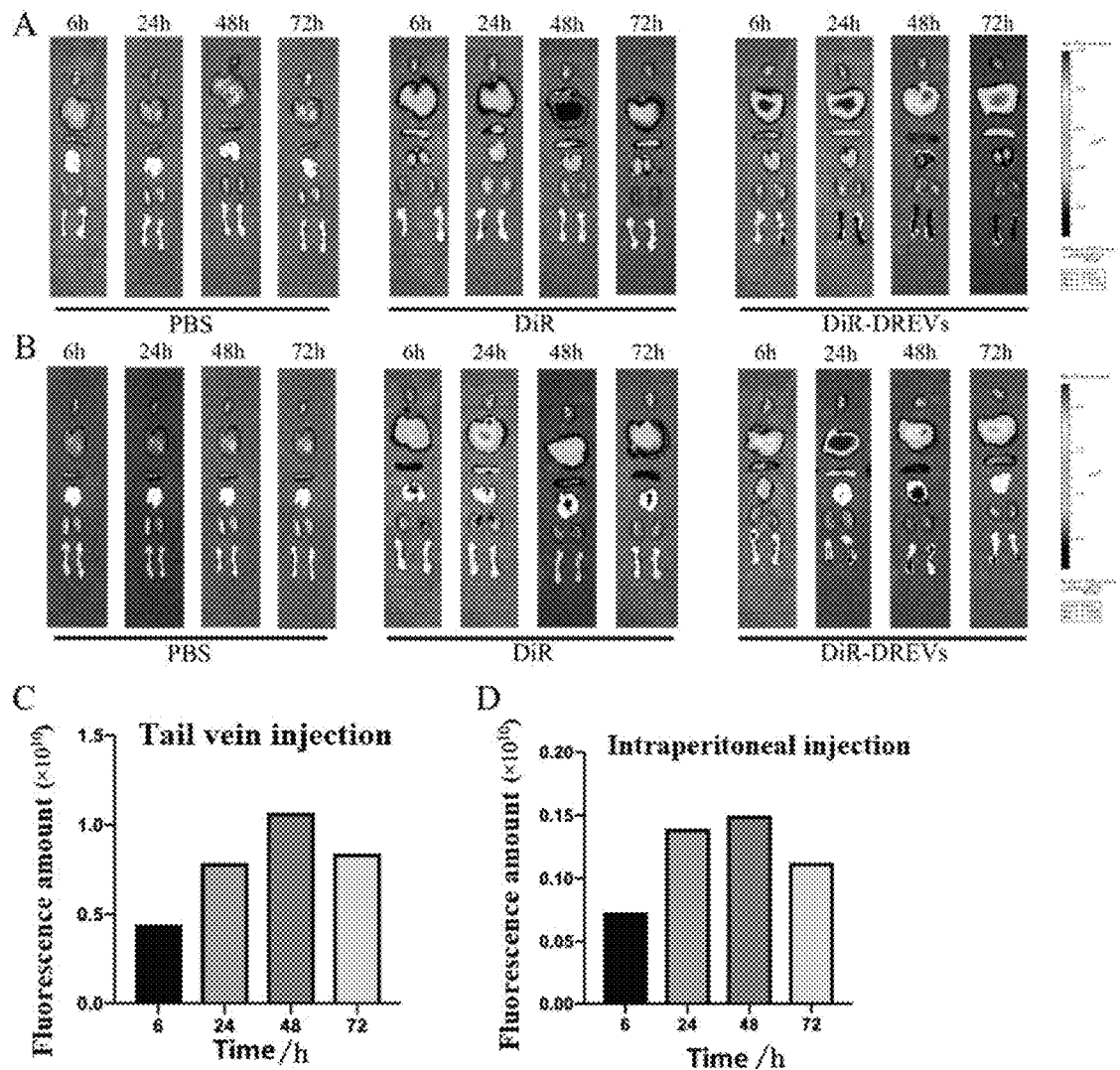
FIG. 8 is a diagram illustrating test results of a bone targeting property of extracellular vesicles of Rhizoma Drynariae in mice, where figure A is a diagram illustrating test results of a bone targeting property of extracellular vesicles of Rhizoma Drynariae in mice through tail vein injection, figure B is a diagram illustrating test results of a bone targeting property of extracellular vesicles of Rhizoma Drynariae in mice through intraperitoneal injection, figure C is a diagram illustrating that amounts of fluorescence in bones of mice vary with time after DiR-DREVs are injected into tail veins, and figure D is a diagram illustrating that amounts of fluorescence in bones of mice vary with time after DiR-DREVs are injected into abdominal cavities.

The results show that in the group of tail vein injection, no signal can be detected at any time point in mice administered PBS, most fluorescence signals detected in mice administered the DiR staining solution are located in livers, spleens and lungs while no signal can be detected in bones, hearts and kidneys, most fluorescence signals detected in mice administered the DiR-DREVs are also located in livers, spleens and lungs while no signal can be detected in hearts and kidneys, but in mice at 6, 24, 48 and 72 hours, corresponding signals can be clearly detected in bones (figure A in FIG. 8). In the group of intraperitoneal injection, no signal can be detected at any time point in mice administered PBS, most fluorescence signals detected in mice administered the DiR staining solution are located in livers and spleens, a small amount of signals are located in lungs, a small amount of signals can be detected in kidneys at a certain time point, while no signal can be detected in bones and hearts; and most fluorescence signals detected in mice administered the DiR-DREVs are also located in livers and spleens, a small amount of signals can be occasionally detected in lungs, while no signal can be detected in hearts and kidneys, but in mice at 6, 24, 48 and 72 hours, corresponding signals can be detected in bones (figure B in FIG. 8).

Then, fluorescence regions of each organ in each group of mice were quantified by using Living Imaging software to obtain corresponding values (the specific data are shown in Table 1 and Table 2).

TABLE 1

Amounts of fluorescence ($\times 10^{10}$) of organs in vivo after tail vein injection of DiR-DREVs

|      | Liver | Spleen | Lung  | Bone   |
|------|-------|--------|-------|--------|
| 6 h  | 15.28 | 1.268  | 3.808 | 0.4428 |
| 24 h | 18.67 | 2.695  | 3.091 | 0.7871 |
| 48 h | 17.82 | 0.213  | 1.297 | 1.0692 |
| 72 h | 20.85 | 2.719  | 2.282 | 0.8407 |

TABLE 2

Amounts of fluorescence ($\times 10^{10}$) of organs in vivo after intraperitoneal injection of DiR-DREVs

|      | Liver | Spleen | Lung   | Bone    |
|------|-------|--------|--------|---------|
| 6 h  | 2.817 | 0.2267 | 0.8914 | 0.07309 |
| 24 h | 4.241 | 0.5766 | /      | 0.13959 |
| 48 h | 3.024 | 0.1236 | 0.1615 | 0.14998 |
| 72 h | 3.688 | 0.5083 | /      | 0.11238 |

The results show that in the group of tail vein DiR-DREVs, the liver is a position distributed with most DiR-DREVs at any time point and the amount of fluorescence in the bone after the tail vein injection of DiR-DREVs shows a trend of gradually increasing and then decreasing with a largest amount of fluorescence at 48 hours (figure C in FIG. 8). Similarly, in the group of abdominal cavity DiR-DREVs, the liver is a position distributed with most DiR-DREVs at any time point and the amount of fluorescence in the bone after the intraperitoneal injection of DiR-DREVs shows a trend of gradually increasing and then decreasing with a largest amount of fluorescence at 48 hours (figure D in FIG. 8). The amount of fluorescence of each organ in the group of tail vein injection of DiR-DREVs is significantly higher than that in the group of intraperitoneal injection of DiR-DREVs.

The above results indicate that the DREVs have the bone targeting property in vivo and the mode of administration has a certain effect on the bone targeting property of the DREVs.

Example 5

Metabolomics Analysis of DREVs

The metabolomics analysis was performed on the DREVs. An experimental method is described below.

1. Pretreatment of DREV Samples
   (1) The DREV samples were lyophilized.
   (2) 400 μL methanol was added, vortexed by using a vortex oscillator for 30 s and sonicated for 3 min. Then, two small steel balls were added, placed at −20° C. for 2 min to be pre-cooled and added to a grinder to be ground for 2 min at 60 Hz.
   (3) The mixture was centrifuged at 13000 rpm for 10 min at 4° C. 350 μL of the treated samples was taken, loaded into a liquid chromatography-mass spectrometry (LC-MS) injection vial and then dried by using a freeze-concentrated centrifugal dryer.
   (4) Redissolving was performed with 300 μL methanol-water (volume ratio of methanol to water=1:4). The solution was vortexed for 30 s, sonicated for 3 min and then allowed to stand for 2 h at −20° C.
   (5) The solution was centrifuged at 13000 rpm for 10 min at 4° C. 100 μL supernatant was drawn by using a syringe, filtered by using a 0.22 μm organic phase pinhole filter, transferred to an LC injection vial and stored at −80° C. until an LC-MS analysis was performed.
   (6) Extracts from all samples were mixed in an equal volume to prepare into a quality control sample (QC), where a volume of the QC was the same as a volume of the samples.

2. On-Machine Detection of the DREV Samples

The DREV samples were loaded on the machine, and non-targeted metabolomics data of the DREV samples were detected by using an LC-MS system composed of an ultra-high-performance liquid tandem QE high-resolution mass spectrometer. Chromatographic conditions: a chromatography column was ACQUITY UPLC HSS T3 (100 mm×2.1 mm, 1.8 μm), and a mobile phase was A-water (containing 0.1% formic acid) and B-acetonitrile (containing 0.1% formic acid) with a flow rate of 0.35 mL/min and a volume of injection of 2 μL. Mass spectrometry conditions: an ion source was ESI, and mass spectrum signals of the samples were acquired in positive and negative ion scan modes, respectively.

3. Data Processing and Analysis

Based on the non-targeted metabolomics data of the ultrahigh-performance liquid tandem high-resolution mass spectrometer, qualitative and relative quantitative analyses were performed on the original data by using metabolomics data processing software Progenesis Q1 v2.3, standardized preprocessing was performed on the original data, and finally, an overall analysis was performed on the data. Effective ingredients of Rhizoma Drynariae were retrieved from Traditional Chinese Medicines Integrated Database (TCMID, http://19.3.41.228: 8000/tcmid/), Traditional Chinese Medicine Systems Pharmacology Database and Analysis Platform (TCMSP, https://icmspw.com/tcmsp.php) and Symptom Mapping (SymMap, http://www.ymmap.org), and the obtained metabolomics ingredients of the DREVs were intersected with the ingredients of Rhizoma Drynariae to obtain common ingredients of the DREVs and Rhizoma Drynariae.

The experimental results are described below.

A total of 3075 metabolites were identified in the DREVs, including a total of 86 flavone and isoflavone metabolites. The classification of Super Class was performed on the 3075 metabolites. The results show that the 3075 metabolites include lipids and lipid molecules (29%), organic oxygen compounds (10%), organic acids and derivatives thereof (9%), organic heterocyclic compounds (9%), phenylpropanoids and polyketides (7%) and benzene ring-type compounds (7%). Then, the classification of Class was performed. The results show that the 3075 metabolites include fatty acyl group (15%), organic oxygen compounds (11%), carboxylic acids and derivatives (8%), isopentenol lipids (8%), glycerophospholipids (7%), benzene and substituted derivatives thereof (4%) and flavone (3%).

To discuss whether the metabolites contained in the DREVs have certain ingredients of the traditional Chinese medicine, a total of 115 effective ingredients of Rhizoma Drynariae were retrieved from TCMSP, TCMID and SysMap database, and an intersection analysis was performed on the 115 effective ingredients of Rhizoma Drynariae and the metabolic ingredients of the DREVs to obtain eleven common ingredients. The eleven common ingredients were sorted from large to small according to relative contents of the ingredients in the DREVs, that is, naringin (flavone), eriodictyol (flavone), cinnamic acid (cinnamic acid and derivatives thereof), naringenin (flavone), prunin (polyketides), caffeic acid (cinnamic acid and derivatives thereof), sinapinic acid (cinnamic acid and derivatives thereof), afzelin (polyketides), secoisolariciresinol (diphenylbutane lignin), narirutin (flavone) and kaempferol (flavone). Among the common ingredients, an ingredient with a highest content is naringin. Naringin has a relative content of 6204781, which ranks first among flavone and isoflavone metabolic ingredients and twenty-third among all metabolic ingredients of the DREVs.

The above results indicate that the DREVs contain some effective ingredients related to Rhizoma Drynariae. Therefore, the DREVs can exert a function similar to Rhizoma Drynariae and have the potential to treat diseases such as OP.

Example 6

Exploring Regulation of ER Pathway by DREVs

20 μg/mL DREVs were co-cultured with h-BMSCs, and changes in the mRNA expression of related genes (ERα and ERβ) of the ER pathway were detected through qRT-PCR.

An experimental method is described below.

The h-BMSCs were purified, cultured, grown to an appropriate density and digested by trypsin, and the cells were collected and counted. The cells were inoculated in a six-well plate according to a cell density of $2\times10^5$ cells/cm$^2$, and the six-well plate was placed in an incubator for continuous culture. When the cell density was increased to 80%, the 20 μg/mL DREVs were taken and co-cultured with the h-BMSCs, which was recorded as an experimental group. In addition, a blank group was set without adding DREVs. After stimulation for 24 h and 48 h, respectively, the cells were collected by using a TRI2ol lysate, placed in sterilized EP tubes and marked, and qRT-PCR was performed to detect the mRNA expression of the related genes (ERα and ERβ) of the ER pathway.

Primer sequences of the related genes are as follows:
Gapdh Sequences:

```
SEQ ID NO. 5:
ACAACTTTGGTATCGTGGAAGG (5'->3')

SEQ ID NO. 6:
CTTTGACACCGCACTACCG (5'->3')
```

ERα Sequences:

```
SEQ ID NO. 7:
GGGAAGTATGGCTATGGAATCTG (5'->3')

SEQ ID NO. 8:
TTGCTGATATACACAGGTCGGT (5'->3')
```

ERβ Sequences:

```
SEQ ID NO. 9:
TTCAAAGAGGGATGCTCACTTC (5'->3')

SEQ ID NO. 10:
CCTCAGACCAGCACACTTCC (5'->3')
```

An amplification reaction method was the same as that in Example 3.

Figure 9:
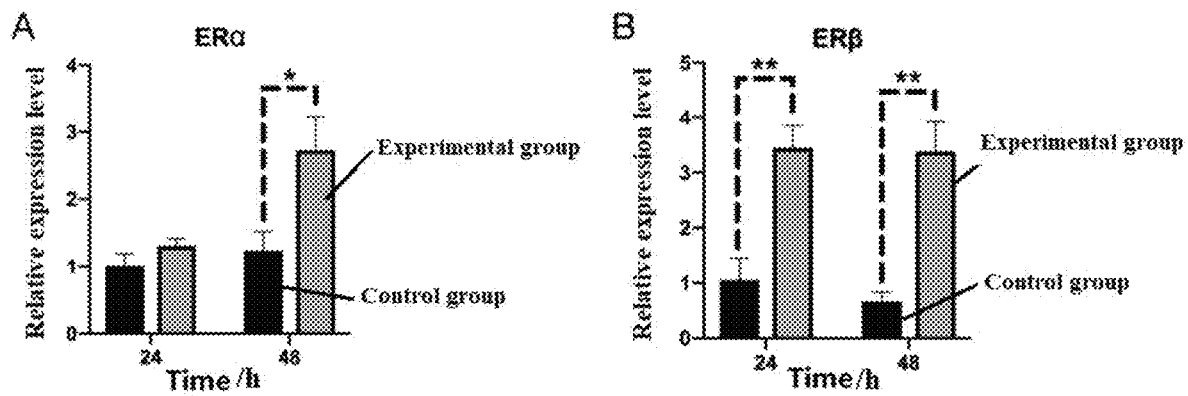
FIG. 9 is a diagram illustrating test results of the regulation of an ER pathway by extracellular vesicles of Rhizoma Drynariae, where figure A is a diagram illustrating results of effects of the extracellular vesicles of Rhizoma Drynariae on the expression of ERα, and figure B is a diagram illustrating results of effects of the extracellular vesicles of Rhizoma Drynariae on the expression of ERβ.

The experimental results are shown in FIG. 9.

As shown in FIG. 9, compared with the control group, a relative expression quantity of ERα in the group of 20 μg/mL DREVs shows an upregulated trend, and a difference at 48 h has a statistical significance (figue A in FIG. 9, $P<0.05$); compared with the control group, a relative expression quantity of ERβ in the group of 20 μg/mL DREVs shows a significantly upregulated trend, and differences at 24 h and 48 h both have a statistical significance (figure B in FIG. 9, $P<0.05$); and an expression quantity of ERβ in each group at 48 h is lower than an expression quantity of ERβ in a corresponding group at 24 h.

The above results indicate that the DREVs can upregulate the mRNA expression of the related genes (ERα and ERβ) of the ER pathway, thereby regulating the ER pathway. Studies have shown that Rhizoma Drynariae can regulate the ER pathway. Therefore, this example further proves that the DREVs have a related function of Rhizoma Drynariae.

The applicant has stated that although the use of the DREVs to the preparation of the medicine for treating the orthopedic disease in the present application are described through the preceding examples, the present application is not limited to the preceding examples, which means that the implementation of the present application does not necessarily depend on the preceding examples. It should be apparent to those skilled in the art that any improvements made to the present application, equivalent replacements of raw materials of the product of the present application, additions of adjuvant ingredients, selections of specific manners, etc., all fall within the protection scope and the disclosure scope of the present application.

Although the preferred embodiments of the present application have been described above in detail, the present application is not limited to details of the above-described embodiments, and various simple modifications can be made to the technical solutions of the present application without departing from the technical concept of the present application. These simple modifications are all within the protection scope of the present application.

In addition, it is to be noted that if not in collision, the specific technical features described in the preceding embodiments may be combined in any suitable manner. In order to avoid unnecessary repetition, the present application does not further specify any of various possible combination manners.

What is claimed is:

1. A method of making extracellular vesicles of Rhizoma Drynariae comprising the following steps:
    (1) juicing fresh Rhizoma Drynariae, filtering, collecting a filtrate, centrifuging to remove impurities and collecting a supernatant; wherein the centrifuging comprises three centrifugations, a first centrifugation performed at a speed of 100-500 g producing a first supernatant, a second centrifugation performed on said supernatant at a speed of 1000-3000 g producing a second supernatant, and a third centrifugation performed at a speed of 8000-12000 g producing a third supernatant; wherein the centrifugations are each independently performed for 5-30 min;
    (2) centrifuging the third supernatant at a speed of 100000-200000 g for 60-120 min, and collecting a precipitate to obtain the extracellular vesicles of Rhizoma Drynariae wherein the extracellular vesicles of Rhizoma Drynariae contains naringin, eriodictyol, cinnamic acid, naringenin, prunin, caffeic acid, sinapinic acid, afzelin, secoisolariciresinol, narirutin and kaempferol.

* * * * *

```
                            SEQUENCE LISTING

Sequence total quantity: 10
SEQ ID NO: 1            moltype = DNA   length = 20
FEATURE                 Location/Qualifiers
misc_feature            1..20
                        note = ALP primer
source                  1..20
                        mol_type = other DNA
                        organism = synthetic construct
SEQUENCE: 1
accaccacga gagtgaacca                                                      20

SEQ ID NO: 2            moltype = DNA   length = 21
FEATURE                 Location/Qualifiers
misc_feature            1..21
                        note = ALP primer
source                  1..21
                        mol_type = other DNA
                        organism = synthetic construct
SEQUENCE: 2
ccctgaccat gagtctgttg c                                                    21

SEQ ID NO: 3            moltype = DNA   length = 21
FEATURE                 Location/Qualifiers
misc_feature            1..21
                        note = BMP2 primer
source                  1..21
                        mol_type = other DNA
                        organism = synthetic construct
SEQUENCE: 3
actaccagaa acgagtggga a                                                    21

SEQ ID NO: 4            moltype = DNA   length = 21
FEATURE                 Location/Qualifiers
misc_feature            1..21
                        note = BMP2 primer
source                  1..21
                        mol_type = other DNA
                        organism = synthetic construct
SEQUENCE: 4
tccaaaaggc tcttgtctac g                                                    21

SEQ ID NO: 5            moltype = DNA   length = 22
FEATURE                 Location/Qualifiers
misc_feature            1..22
                        note = GAPDH primer
source                  1..22
                        mol_type = other DNA
                        organism = synthetic construct
SEQUENCE: 5
acaactttgg tatcgtggaa gg                                                   22

SEQ ID NO: 6            moltype = DNA   length = 19
FEATURE                 Location/Qualifiers
misc_feature            1..19
                        note = GAPDH primer
source                  1..19
                        mol_type = other DNA
                        organism = synthetic construct
SEQUENCE: 6
ctttgacacc gcactaccg                                                       19

SEQ ID NO: 7            moltype = DNA   length = 23
FEATURE                 Location/Qualifiers
misc_feature            1..23
                        note = ER alpha primer
source                  1..23
                        mol_type = other DNA
                        organism = synthetic construct
SEQUENCE: 7
gggaagtatg gctatggaat ctg                                                  23

SEQ ID NO: 8            moltype = DNA   length = 22
```

```
FEATURE              Location/Qualifiers
misc_feature         1..22
                     note = ER alpha primer
source               1..22
                     mol_type = other DNA
                     organism = synthetic construct
SEQUENCE: 8
ttgctgatat acacaggtcg gt                                              22

SEQ ID NO: 9         moltype = DNA  length = 22
FEATURE              Location/Qualifiers
misc_feature         1..22
                     note = ER beta primer
source               1..22
                     mol_type = other DNA
                     organism = synthetic construct
SEQUENCE: 9
ttcaaagagg gatgctcact tc                                              22

SEQ ID NO: 10        moltype = DNA  length = 20
FEATURE              Location/Qualifiers
misc_feature         1..20
                     note = ER beta primer
source               1..20
                     mol_type = other DNA
                     organism = synthetic construct
SEQUENCE: 10
cctcagacca gcacacttcc                                                 20
```